United States Patent [19]
Jeromin et al.
[11] Patent Number: 4,719,298
[45] Date of Patent: Jan. 12, 1988

[54] SIDE CHAIN CHLORINATION PROCESS OF HETEROCYCLES

[75] Inventors: Günter E. Jeromin, Heidelberg; Winfried Orth, Hassloch/Pfalz; Werner Fickert, Mannheim, all of Fed. Rep. of Germany

[73] Assignee: Rutgerswerke Aktiengesellschaft, Fed. Rep. of Germany

[21] Appl. No.: 853,630

[22] Filed: Apr. 18, 1986

[30] Foreign Application Priority Data

May 30, 1985 [DE] Fed. Rep. of Germany ....... 3519364

[51] Int. Cl.[4] .................... C07B 39/00; C07D 241/42; C07D 213/26; C07D 215/12

[52] U.S. Cl. .................................... 544/182; 260/694; 544/216; 544/224; 544/242; 544/336; 544/353; 546/101; 546/139; 546/180; 546/346

[58] Field of Search ................ 260/694; 544/190, 191, 544/353, 182, 216, 224, 242, 336; 546/180, 346, 139, 101

[56] References Cited

PUBLICATIONS

Ziegler et al., *Ann.* 551, 80 (1942).
Juenge et al., *J. Org. Chem.* 35, 719 (1970).
Mura et al., *Tet. Lett.* 50, 4433 (1975).

*Primary Examiner*—Mark L. Berch
*Assistant Examiner*—Emily Bernhardt
*Attorney, Agent, or Firm*—Bierman & Muserlian

[57] ABSTRACT

A novel method of chlorinating the alkyl side chains of a nitrogen containing heterocyclic comprising reacting an alkyl substituted heterocycle with trichloroisocyanuric acid at temperatures of 20° to 200° C. to obtain the same in high yields.

5 Claims, No Drawings

SIDE CHAIN CHLORINATION PROCESS OF HETEROCYCLES

STATE OF THE ART

Chlorination of methyl-pyridines with chlorine is known to be difficult and leads to only low yields of chloromethyl pyridines because hydrogen chloride formed in the reaction inhibits the desired chlorination. German Pat. No. 1,204,231 attempted to circumvent this difficulty by adding an acid binding agent such as dry sodium carbonate to the reaction mixture. A similar solution was proposed in Japanese Application No. 74-127977. Another solution proposed in French Pat. No. 1,394,362 effected side chain chlorination of alkyl-pyridines with chlorine in the presence of concentrated or fuming sulfuric acid and a radical former such as azoisobutyric acid nitrile or ultraviolet light whereby the extremely high acid concentration prevents chlorination of the pyridine nucleus.

The said processes, however, have disadvantages since chlorine is toxic, difficult to handle and to control its addition. The French patent uses large amounts of sulfuric acid which creates disposal problems and requires a large amount of expensive azoisobutyric acid nitrile.

OBJECTS OF THE INVENTION

It is an object of the invention to provide a novel simple and economical process for chlorination of alkyl side chains of nitrogen heterocycles free of the disadvantages of the prior art.

This and other objects and advantages of the invention will become obvious from the following detailed description.

THE INVENTION

The novel process of the invention of chlorinating the alkyl side chain of a nitrogen containing heterocyclic comprising reacting an alkyl substituted heterocycle with trichloroisocyanuric acid at temperatures of 20° to 200° C. to obtain the chloroalkyl heterocycle. The alkyl side chain is easily and selectively chlorinated in ordinary organic solvents inert under the reaction conditions with trichloroisocyanuric acid.

The use of trichloroisocyanuric acid as chlorinating agent is known. In J. Org. Chem. Vol. 31, page 3836–3838 (1966), it was used for the chlorination of cyclic ethers and in Ann. Vol. 551, Page 80 (1942) it was used for the chlorination of cyclohexene. Also it is known from J. Org. Chem. Vol. 35, Page 719 (1970) to use trichloroisocyanuric acid for the chlorination of aromatic hydrocarbons. But a clear distinction is made here between acid-catalyzed nucleus-chlorination and side-chain chlorination catalyzed by a radical former such as benzoyl peroxide or the chlorination of naphthalene without catalyst to a nucleus-chlorinated product.

It is surprising that the chlorination of alkyl nitrogen heterocycles can occur with trichloroisocyanuric acid because chlorination with known and per se common N-chlorosuccinimide without a catalyst proceeds negatively in this class of compounds. One skilled in the art would expect therefore, that the reaction of trichloroisocyanuric acid with 2-methyl pyridine for instance without a radical chain initiator would either lead to no reaction or to a nucleus chlorination reaction.

Another advantage of the method of the invention is that the alkyl group containing N-heterocycles react spontaneously with trichlorisocyanuric acid to form the chlorinated compounds with good yields. Here the chlorination takes place in the side chain and nucleus-chlorinated products are practically not detectable, although they were to be expected since cyanuric acid forming in the reaction could very well catalyze a chlorination of the nucleus.

What takes place at first is a monochlorination and with an excess of chlorinating agent a polychlorination of the already chlorinated alkyl group. The method is suitable particularly for alkyl heterocycles with 1 to 3 carbon atoms in the alkyl which possess the alkyl group adjacent to the hetero atom. For example, $\alpha$-picoline chlorinates easily, gamma-picoline with a lower yield, and $\beta$-picoline almost not at all.

The method excels by its simplicity of execution, low toxicity, and good handling and dosability of the chlorinating agent and its consequent product. In particular, acid-sensitive compounds such as picolines can be chlorinated advantageously and addition of bases is not necessary as hydrogen chloride is not formed. Also, the processing of the reaction mixture is quite simple. The reaction can advantageously be conducted by adding the alkyl-heterocycle to be chlorinated to a suitable solvent and adding the trichloroisocyanuric acid at the selected temperature in portions, or by charging the chlorinating agent in the solvent and adding the alkyl heterocycle to be chlorinated. Also, in the case of relatively small batches, the alkyl heterocycle, the chlorinating agent and the solvent can be admixed at room temperature and slowly heated until the reaction starts. The reaction can be carried out at 20° to 200° C., preferably at 40° to 100° C. Lower reaction temperatures require longer reaction times and higher temperatures lead to higher chlorinated products more quickly.

To facilitate the start of the reaction, an acid amide such as dimethylformamide, acetamide or benzamide may be added to the reaction mixture in small amounts such as 1 to 10% by weight based on the weight of the heterocycle. This addition is not absolutely necessary for the conduction of the chlorination, but may be helpful in many cases and may give better yields.

Compounds to be chlorinated by the invention are nitrogenous heterocycles which possess one or more alkyls of 1 to 3 carbon atoms as side chains, with the side chain being preferably in $\alpha$-position to the nitrogen atom. As nitrogenous heterocycles may serve all basic substances which have a quasi-aromatic molecule such as pyridine, pyridazine, pyrimidine, pyrazine, quinoline, triazine, isoquinoline, quinoxaline or benzoquinoline. The alkyl-substituted nitrogen heterocycles in the reaction are dissolved in a solvent which under the conditions of the reaction is inert to trichloroisocyanuric acid. Examples of such solvents are methylene chloride, trichloromethane, tetrachloromethane, dichloroethane, trichloroethane, benzene, chlorobenzene, dimethyl formamide, alkanes and cycloalkane.

The trichloroisocyanuric acid used may be the pure compound or a technical grade. For the chlorination reaction, two chlorine atoms are available so that theoratically one could also employ dichloroisocyanic acid as chlorinating agent. The amount of trichloroisocyanuric acid used depends on the desired degree of chlorination, and it is a further advantage of the method of the invention that when stoichiometric quantities of alkyl-substituted N-heterocycles and trichloroisocyanuric acid are used, only a monochlorination occurs. Only with greater quantities of trichloroisocyanuric acid are the monochlorine products chlorinated to di- or tri-chlorine products.

In the following examples there are described several preferred embodiments to illustrate the invention. However, it should be understood that the invention is not intended to be limited to the specific embodiments.

EXAMPLE 1

2-chloromethyl-pyridine

A mixture of 200 g (2.15 moles) of α-picoline and 7 g of benzamide in 750 ml of chloroform was refluxed and 270 g (1.16 mole) of trichlorisocyanuric acid (min. 90% available chlorine) were added thereto in portions over 5 hours. The mixture was stirred for another 5 hours and then cooled. 1200 ml of water and 400 g of 50% potassium hydroxide were added to the mixture with stirring. The decanted aqueous phase was extracted with 250 ml of chloroform, and the combined chloroform phases were dried over $MgSO_4$ and carefully evaporated at 30° C. under reduced pressure to obtain 181 g of 2-chloromethyl-pyridine (66% yield) with a boiling point of 77°-82° C. at 15 mm Hg which quickly turned red.

EXAMPLE 2

2-chloromethyl-pyridine hydrochloride

A solution of 200 g (2.15 moles) of 2-methyl-pyridine and 14 g of dimethylformamide in 750 ml chloroform was heated at reflux while 300 g (1.29 mole) of trichloroisocyanuric acid (min. 90% available chlorine) were added thereto in portions without heating over 50 minutes as the reaction mixture remained under reflux by itself. The mixture was stirred for another 2 hours and was cooled and vacuum filtered. The filtrate was washed with 100 ml of 5% sodium hydroxide and the chloroform phase was dried over $MgSO_4$, and filtered. 100 g (2.74 moles) of dry hydrogen chloride were added to the filtrate which was evaporated to dryness under vacuum. The residue was added to 250 ml of dry acetone and the mixture was stirred and vacuum filtered. The precipitate was washed with a little acetone and dried to obtain 185 g of 2-chloromethyl-pyridine hydrochloride. The acetone solution was cooled in the refrigerator to obtain another 42 g product for a total yield of 227 g (64.4%) melting at 120° to 122° C.

| Analysis: | Total Chlorine | Chloride |
|---|---|---|
| Calculated | 43.22% | 21.61% |
| Found | 43.92% | 21.41% |

EXAMPLE 3

2-chloromethyl-3-methyl pyridine

A mixture of 107.16 g (1 mole) of 2,3-dimethyl-pyridine and 5 g of benzamide in 400 ml of cyclohexane was heated to reflux while adding over 4 hours 130 g (0.56 mole) of trichloroisocyanuric acid (min. 90% available chlorine) in portions and the mixture was stirred for another 7 hours at reflux and then cooled. Under agitation mix with 500 ml of water and 150 ml of 50% potassium hydroxide were added with stirring to obtain a solution. The decanted organic phases were dried over $MgSO_4$ and evaporated to dryness under reduced pressure to obtain 85 g (60%) of 2-chloromethyl-3-methyl pyridine which slowly colored red with a boiling point of 53° to 57° C. at 3 mm H

EXAMPLE 4

2-chloromethyl quinoline

A solution of 143.19 g (1 mole) of quinaldine in 350 ml of chloroform was heated to 60° C. and 83 g (0.36 mole) of trichloroisocyanuric acid (min. 90% available chlorine) were added thereto in portions over 175 minutes. The mixture was stirred for another 45 minutes at 60° C. and then cooled. 700 ml of water and 200 ml of 50% potassium hydroxide were added with stirring until two clear layers have formed. The decanted aqueous phase was extracted twice with 150 ml of chloroform and the combined chloroform phases were covered with a layer of 350 ml of 10% HCl to thoroughly extract any 2-monochloromethyl-quinoline from the chloroform solution. The decanted chloroform phase was dried over $MgSO_4$ and evaporated to dryness on a rotary evaporator to obtain 52 g (24.5%) of crude dichloromethyl-quinoline. After recrystallization from isopropanol, there were 16 g (7.5%) of product melting at 80° to 81° C. with a chlorine content of 33.02% (theory 33.4%). The acid aqueous phase was covered with 300 ml of ethyl acetate and the pH was adjusted to 3 with 50% sodium hydroxide. The mixture was well stirred and the decanted aqueous phase was extracted with 100 ml of ethyl acetate again. The combined acetic ester phases were dried over $MgSO_4$ and evaporated to dryness to obtain 95 g (53.5%) of crystalline 2-chloromethylquinoline melting at 53° C. with a chlorine content of 19.87% (theory 19.96%). The aqueous phase was made alkaline with sodium hydroxide and was extracted with 200 ml of ethyl acetate. After drying and evaporating the organic phase, 23 g of quinaline were recovered. The yield of 2-chloromethyl-quinoline calculated for reacted quinaldine was 63.7%.

EXAMPLE 5

2-(1-chloroethyl)-pyridine

A solution of 107.16 g (1 mole) of 2-ethyl-pyridine in 400 ml of ethylene chloride was heated at reflux while adding in portions 150 g (0.65 mole) of trichloroisocyanuric acid (min. 90% available chlorine) over 5 hours and the mixture was stirred for another 2 hours and then cooled and vacuum filtered. The filtrate was washed with 50 ml of 5% of potassium hydroxide, dried over $MgSO_4$ and evaporated to dryness.

53.5 g of crude product with a boiling point of 45° to 50° C. at 0.5 mm Hg were dissolved in 150 ml of chloroform and the solution was extracted with 150 g of 10% HCl. The acid phase was neutralized to a pH of 4 with sodium hydroxide and was extracted with 150 ml of ethyl acetate. After drying and evaporating to dryness, 35.5 g (25.1%) of 2-(1-chloroethyl)-pyridine with a chlorine content of 25.73% (theory 25.04%) were obtained.

EXAMPLE 6

2-chloromethyl-quinoxaline

A solution of 72.1 g (0.5 mole) of 2-methyl-quinoxaline in 250 ml of chloroform was heated at reflux while adding with stirring 52 g (0.22 mole) of trichloroisocyanuric acid (min. 90% available chlorine) over 90 minutes in portions. Stirring was continued for another 30 min. and after cooling, 350 ml of iced water were added. The mixture was made alkaline with cooling at 5° to 10° C. by addition of 65 ml of 50% potassium hydroxide. The decanted phase was extracted with 100 ml of chloroform and the combined chloroform phases were dried and evaporated to dryness to obtain 88 g of yellow crystals. The crude product was crystallized from 70 ml of n-hexane to obtain 67 g (75%) of 2-chloromethyl-quinoxaline melting at 45° to 46° C. (decomposition).

Analysis: Calculated: %C 60.52; %H 3.95; %N 15.68; %Cl 19.85%; Found: 59.9; 3.8; 15.5; 19.97%.

EXAMPLE 7

2-chloromethyl-4,6-dimethyl-pyridine

A solution of 121.18 g (1 mole) of 2,4,6-collidine in 400 ml of chloroform was heated at reflux while adding in portions 140 g (0.6 mole) of trichloroisocyanuric acid (min. 90% available chlorine) over 4 hours and stirring was continued for another 30 minutes and then cooled and filtered. The filtrate was admixed with 150 ml of 10% HCl to transform the product into the aqueous phase. The decanted acid aqueous phase was mixed with 150 ml of ethyl acetate and was made alkaline with sodium hydroxide. The decanted aqueous phase was extracted with 100 ml of ethyl acetate. The organic phase was dried and evaporated to dryness under reduced pressure to obtain 45 g (28.9%) of 2-chloromethyl-4,6-dimethyl pyridine with a Cl content of 22.78% (theoretical 22.78%) and a boiling point of 64° to 70° C. at 1 mm Hg.

COMPARISON EXAMPLE

Attempted chlorination with N-chlorosuccinimide 200 g (2.15 moles) of 2-methyl-pyridine were dissolved in 750 ml of chloroform and heated at reflux while adding 287.1 g (2.15 moles) of N-chlorosuccinimide (98% active chlorine) in portions over 5 hours and the mixture was then heated for another 5 hours at reflux. No appreciable reaction was observed by thin layer chromatography.

Various modifications of the process of the invention may be made without departing from the spirit or scope thereof and it should be understood that the invention is intended to be limited only as defined in the appended claims.

What we claim is:

1. A method of chlorinating alkyl side chains of nitrogen heterocycles consisting essentially of reacting an α-alkyl side chain quasi aromatic nitrogen heterocycle in an inert solvent with trichloroisocyanuric acid at 20° to 200° C. whereby the side chain carbon atom attached to the nitrogen heterocycle is chlorinated.

2. The process of claim 1 wherein the temperature is 40° to 100° C.

3. The process of claim 1 wherein 1 to 10% by weight of a carboxamide selected from the group consisting of dimethylformamide, acetamide and benzamide based on the weight of the heterocycle is added.

4. The process of claim 1 wherein the amount of heterocycle and trichloroisocyanuric acid is approximately stoichiometric for monochlorination.

5. The method of claim 1 wherein the α-alkyl side chain quasi-aromatic nitrogen heterocycle is selected from the group consisting of pyridine, pyridazine, pyrimidine, pyrazine, quinoline, triazine, isoquinoline, quinoxaline and benzoquinoline, all having an α-alkyl side chain.

* * * * *